United States Patent [19]

Stinnette

[11] Patent Number: 4,607,746
[45] Date of Patent: Aug. 26, 1986

[54] PACKAGING TUBE

[75] Inventor: Russell A. Stinnette, Plantation, Fla.

[73] Assignee: Cordis Corporation, Miami, Fla.

[21] Appl. No.: 779,957

[22] Filed: Sep. 25, 1985

[51] Int. Cl.⁴ .................................. B65H 75/28
[52] U.S. Cl. .................................. 206/53; 53/430;
220/23.4; 242/159; 242/172
[58] Field of Search ............... 206/53, 55; 220/23.4;
242/159, 172; 53/430, 116, 204

[56] References Cited

U.S. PATENT DOCUMENTS

| 764,779 | 7/1904 | Stone . | |
|---|---|---|---|
| 1,168,909 | 1/1916 | Rook, Jr. . | |
| 2,577,120 | 12/1951 | Franz . | |
| 2,804,973 | 9/1957 | Buddecke | 242/172 X |
| 2,916,055 | 12/1959 | Brumbach . | |
| 3,526,934 | 9/1970 | Owen, Sr. . | |
| 3,587,657 | 6/1971 | Staller . | |
| 3,654,049 | 4/1972 | Ausnit | 206/53 |
| 3,895,708 | 7/1975 | Jureit et al. | 206/53 |
| 3,955,777 | 5/1976 | Burdorf | 206/53 X |
| 4,023,596 | 5/1977 | Tate . | |
| 4,046,408 | 9/1977 | Ausnit . | |
| 4,529,148 | 7/1985 | Hesprich et al. | 242/159 |
| 4,534,522 | 8/1985 | Spence | 242/172 |

FOREIGN PATENT DOCUMENTS 486951 11/1953 Italy .................................. 53/116

Primary Examiner—James F. Coan
Attorney, Agent, or Firm—George H. Gerstman

[57] ABSTRACT

A tube for packaging elongated, flexible members such as a flexible guidewire for medical purposes or the like. The tube comprises a flexible tube body capable of being coiled and having a projecting member extending outwardly from the tube body longitudinally along at least a substantial portion of the length of the tube body. A concave member extends along at least a substantial portion of the tube body in a diametrically opposed position from the projecting member. The concave member is positioned and preportioned to receive the projecting member of another portion of the tube in retentive relation when the tube is coiled.

10 Claims, 2 Drawing Figures

PACKAGING TUBE

BACKGROUND OF THE INVENTION

The packaging of long, thin items such as guide wires for medical purposes or the like presents difficulties. examples of such items include guide wires used with vascular catheters in angiography, and pervenous leads used with a cardiac pacer in cardiac stimulation. For example, guide wires may be as thin as 0.025 inch in diameter, while being 150 cm. in length. Likewise, pervenous leads may be 0.0105 inch in diameter, for example, and 62 cm. in length.

It is desirable for guide wires to be presented for use in unkinked form. Therefore the guide wires cannot be folded into a series of lengths or the like.

One method of packaging guide wires and the like is to insert them into flexible tubing which is only slightly longer than the guidewire itself. The tubing, containing the guidewire, is coiled, and a clip is placed on the tubing coils so that the coil will not unwind, and also so that the coiled package will remain flat.

Alternatively, the guidewire may be coiled, tied and then placed in a package.

In another package design, a preformed tray is used, with the guidewire being coiled in a cavity defined in the performed tray, and a removable cover placed on the tray.

The packaging of such long, thin items as a guidewire is relatively difficult and labor intensive. Likewise, storage of preformed trays consumes additional space, and the stocking of various lengths of tubing in preformed packages can be complicated.

In accordance with this invention, a new packaging system is provided which exhibits substantial advantages, in that less labor is required for inserting the elongated wire members or the like into the package. Likewise stocking is simplified, and the completed package is small and space saving.

DESCRIPTION OF THE INVENTION

In accordance with this invention, a tube for packaging elongated, flexible members is provided. The tube comprises a flexible tube body capable of being coiled. A projecting member extends outwardly from the tube body and longitudinally along at least a substantial portion of the length of the tube body. A concave member extends along a substantial portion of the tube body in a diametrically opposed position from the projecting member. The concave member is positioned and proportioned to receive the projecting member of another portion of the tube in retentive relation when the tube is coiled.

The tubing may be of substantially uniform cross section along substantially its entire length, being for example a length of extruded tubing.

The projecting member may preferably define the shape of an arrowhead in cross section, while the concave member may preferably be C-shaped in cross section.

As stated above, such tubing is desirably used for carrying a flexible guidewire in its interior, being an effective and convenient structure for packaging of guidewires and the like.

DESCRIPTION OF SPECIFIC EMBODIMENT

Figure 2:
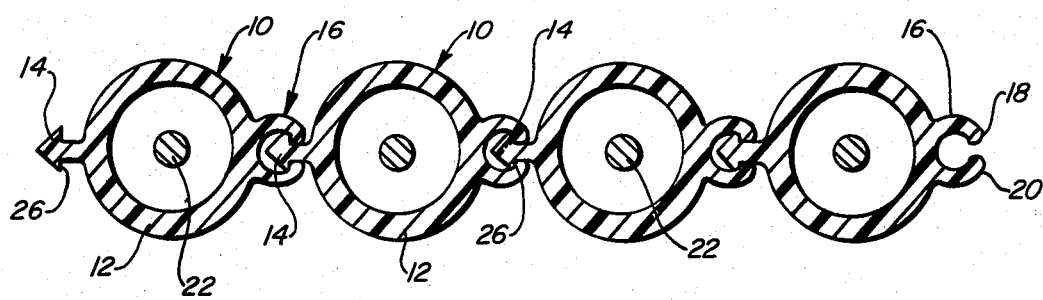
FIG. 2 is an enlarged sectional view taken along line 2—2 of FIG. 1.

Referring to the drawings, tubing 10, which is shown in cross section in FIG. 2, may be extruded by conventional means, for example over an air mandrel. Tubing 10 may be made of any desired flexible, plastic material, for example polyethylene.

As shown, tubing 10 defines a flexible tube body 12 and a projecting member 14 extending outwardly from tube body 12, longitudinally along the length of tube body 12 to form a thin, flange-like structure on one side of tube body 12.

On the other side of tube body 12, in typically diametrically opposed relation to projecting member 14, is concave member 16 which is shown to be a structure of C-shaped cross section, defining a pair of projecting flanges 18, 20, which project inwardly toward each other. Concave member 16 also extends along the length of tube body 12. The cross sectional shape of tubing 10 is governed by the extrusion die from which it is formed, although other techniques than extrusion may be used if desired.

Tubing 10 may be cut to the desired length, typically slightly in excess of the length of the guidewire or other elongated member that tubing 10 is to carry. Guidewire 22 may then be fed into tubing 10. At some point of the process, either before or after loading guidewire 22 into tubing 10, one end 24 of tubing 10 may be closed by transverse heat sealing or the like. The other end of tubing 10 may be closed with a removable plug 26. The positions of heat sealed line 24 and plug 26 may be reversed, if desired. Alternatively, both ends may be plugged or heat sealed as may be desired.

Figure 1:
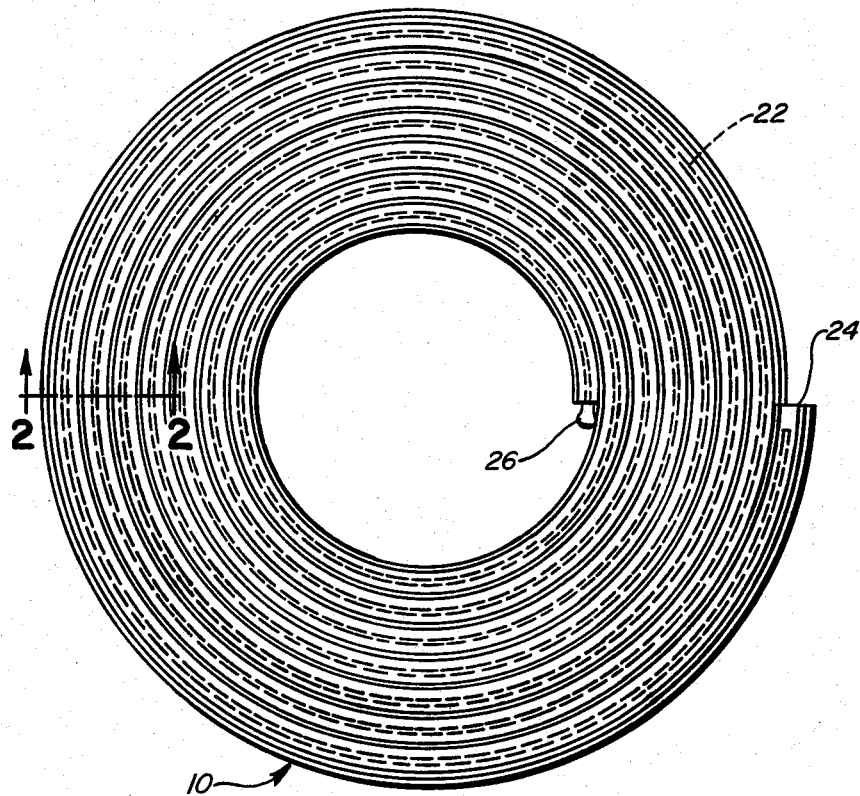
FIG. 1 is a plan view of a coiled tubular package in accordance with this invention.

Following this, the manufacturer can wind tubing 10 on a reel or the like into a coil as shown in FIG. 1, where the individual coils are pressed against each other with some force. As the result of this force, the various portions of the elongated, projecting member 14 press into elongated, concave member 16 of other coils of tubing 10, so that flanges 18, 20 snap into locking relation behind prongs 26 of projecting member 14, which may preferably be of the shape of an arrowhead in cross section. Accordingly, the coiled tubing 10, containing guidewire 22 in sealed relation, may then be removed from the winder and packaged, without the need of tying the coils of tubing together. They may be self-adherent to hold the coil in the desired, coiled relation until the contents are to be used. Then, if desired, tubing 10 may be uncoiled, or, alternatively, one of the ends of tubing 10 may be opened without uncoiling, and the elongated guidewire or other product removed by pulling with a pair of tweezers or the like.

Thus an improved package for flexible, elongated members is provided, eliminating the need for tying the package into a coiled relationship, and thus providing significant cost savings in the packaging of guidewires and other elongated members.

The above has been offered for illustrative purposes only, and is not intended to limit the scope of the invention, which is as defined in the claims below.

That which is claimed is:

1. A tube for packaging elongated, flexible members, which tube comprises: a flexible tube body capable of being coiled; a projecting member extending outwardly from said tube body and longitudinally along at least a substantial portion of the length of said tube body; and a concave member extending along at least a substantial portion of said tube body in a diametrically opposed position from said projecting member, said concave member being positioned and proportioned to receive said projecting member of another portion of said tube in retentive relation when said tube is coiled.

2. The tube of claim 1 which is of substantially uniform cross section along its length.

3. The tube of claim 1 which is extruded in its manufacture.

4. The tube of claim 1 in which said projecting member defines the shape of an arrowhead in cross section.

5. The tube of claim 1 in which said concave member is C-shaped in cross section.

6. The tube of claim 1 which carries a flexible guidewire in its interior.

7. A tube for packaging elongated, flexible members, which tube comprises:
   a flexible tube body capable of being coiled, said tube body being of substantially uniform cross section along its length;
   a projecting member extending outwardly from said tube body and longitudinally therealong, said projecting member defining the shape of an arrowhead in cross section; and
   a concave member extending along the length of said tube body in a diametrically opposed position from said projecting member, said concave member being positioned and proportioned to receive said projecting member of another portion of said tube in retentive relation when said tube is coiled.

8. The tube of claim 7 in which said concave member is C-shaped in cross section.

9. The tube of claim 8 which carries a flexible guidewire in its interior.

10. The tube of claim 9 which is extruded in its manufacture.

* * * * *